United States Patent [19]

Leyerer et al.

[11] Patent Number: 5,642,096

[45] Date of Patent: Jun. 24, 1997

[54] DEVICE FOR PREVENTION OF ULCERS IN THE FEET OF DIABETES PATIENTS

[75] Inventors: Roland Leyerer, Kolbermoor; Peter Schaff, Munich; Oliver Wetter, Raubling, all of Germany

[73] Assignee: Paromed Medizintechnik GmbH, Neubeuern, Germany

[21] Appl. No.: 622,062

[22] Filed: Mar. 26, 1996

Related U.S. Application Data

[63] Continuation-in-part of Ser. No. 33,395, Mar. 19, 1993.

[30] Foreign Application Priority Data

Mar. 20, 1992 [DE] Germany .............. 92037887 U

[51] Int. Cl.⁶ .................................................. A61B 5/00
[52] U.S. Cl. ................. 340/573; 128/736; 128/779; 73/172
[58] Field of Search ................ 340/573; 128/736, 128/779; 73/172

[56] References Cited

U.S. PATENT DOCUMENTS

| | | | |
|---|---|---|---|
| 3,791,375 | 2/1974 | Pfeiffer | 128/779 |
| 3,974,491 | 8/1976 | Sipe | 340/573 |
| 4,554,930 | 11/1985 | Kress | 128/779 |
| 4,647,918 | 3/1987 | Goforth | 73/172 |
| 4,858,620 | 8/1989 | Sugarman | 128/779 |
| 5,033,291 | 7/1991 | Pudoloff | 73/172 |
| 5,230,249 | 7/1993 | Sasaki | 73/172 |
| 5,253,654 | 10/1993 | Thomas | 73/172 |
| 5,546,955 | 8/1996 | Wilk | 128/779 |

*Primary Examiner*—Thomas Mullen
*Assistant Examiner*—Albert Wong
*Attorney, Agent, or Firm*—Morrison Law Firm

[57] ABSTRACT

A device for prevention of ulcers in the feet of diabetes patients is embodied in a footwear article such as in a shoe. The device includes a sensor disposed in a contained liquid mass of a hydrocell carried in the shoe inner sole, the sensor being one that detects both pressure and temperature values to which the patient's feet are exposed. The sensor includes a bridge circuit comprised of four piezoresistors arranged in two diagonally arrayed pairs, the resistance of one pair of resistors increasing and the resistance of the second pair decreasing in the presence of an increase in the pressure condition in the hydrocell, the resistance of all the resistors increasing or decreasing responsive to respective increases and decreases of temperature in the hydrocell. Outputs from the bridge circuit denotive of respective pressure and temperature values are acquired by a warning signal generator to operate same to generate a patient discernible warning signal that indicates to the patient a need to take action to avoid continuance of exposure to the condition. A grid array sensor detects localized pressure changes on the bottom of the foot by reducing the resistance between conductors present at the location of the increases pressure. The decreased resistance causes an increase in current flow between the conductors which is detected by a processor which in turn provides an indication of the increased pressure condition.

10 Claims, 5 Drawing Sheets

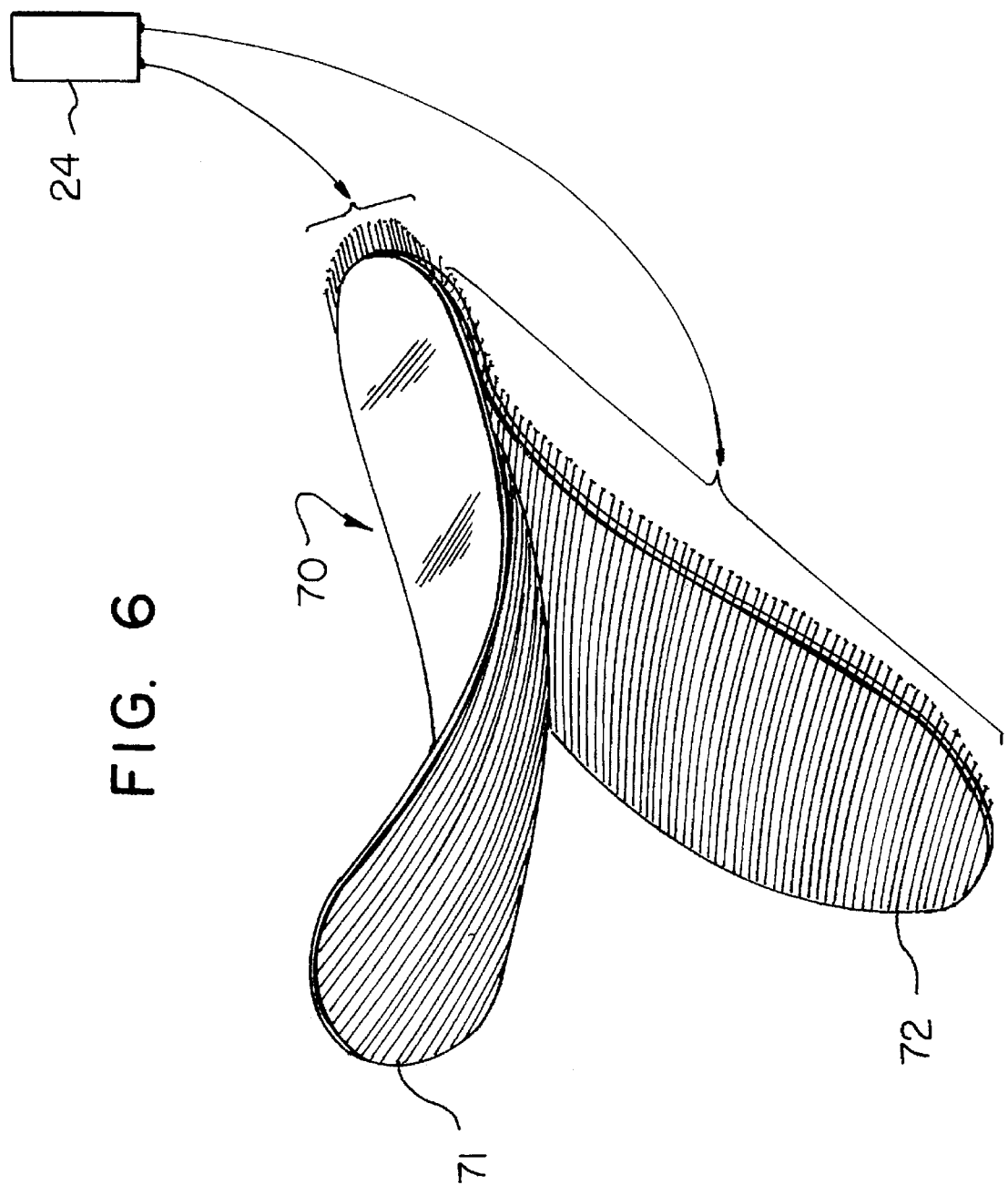

DEVICE FOR PREVENTION OF ULCERS IN THE FEET OF DIABETES PATIENTS

This application is a continuation-in-part of pending application Ser. No. 08/033,395, filed Mar. 19, 1993.

BACKGROUND OF THE INVENTION

The present invention relates to a device for prevention of ulcers in the feet of diabetes patients and, more particularly, to such type of device that functions to detect and signal to the patient presence of adverse pressure and temperature conditions affecting the feet.

In severe forms of diabetes, a diabetes patient can suffer a partial or complete loss of feeling in the lower extremities and especially in the feet. Commonly, the patient fails to notice or be made aware when individual points of a foot are subjected to severe constant pressure condition, for example during long periods of standing. Prolongation and repetition of that condition can lead to development of pressure sores and open wounds, which can become inflamed and easily ulcerated. In addition, small sharp objects can enter a shoe and present a danger of cutting the patients feet without any indication to the patient because of the partial or complete loss of feeling in the feet. Since metabolism and blood circulation already are reduced in diabetes patients, healing of such sores is most difficult. Therapy for dealing with the sores depends on the severity of a wound and the patient's blood circulation condition. But generally, therapy will dictate that a patient's feet be exposed to as little stress as possible and that the patient be aware of the exposure so that the condition be removed.

Therapy also includes prevention of pressure sores and wounds so that a patient who might not be able to recognize existence of a severe sore inducing condition can get off his or her feet to eliminate the condition and reduce the risk of onset of sore development.

Devices are known in the prior art for indicating to a diabetes patient that their feet are being exposed to an excessive stress condition.

U.S. Pat. No. 4,647,918 discloses a shoe insert which is provided with a number of pressure sensors connected by cables with an evaluation device, the evaluation device measuring stress periods and values and making evaluation of these according to prescribed requirements. The device gives discernible warning to a patient but the device is complex and expensive so that its use is limited to a small group of patients.

U.S. Pat. No. 4,813,436 discloses a system for analyzing a person's walking gait. The system includes use of sensors in an inner sole that are connected to processor apparatus so that pressures to which a person's foot is exposed during walking or running can be recorded.

U.S. Pat. No. 5,042,504 discloses a device for monitoring loads imposed on a human body, such monitoring including of the feet. Sensors placed under the sole of a person are used to acquire data, via microprocessing, regarding loadings placed on the feet, this data being recorded to provide a history of the loadings etc that is useful to a physician who may be treating a patient's feet disorder.

European Published Application EP 0 136 247 discloses a device wherein a number of liquid cells are arranged below the sole of a foot inside a shoe, these being connected with tubes to a sleeve wrappable about a person's calf below the knee. When pressure is brought to bear on the liquid cells, i.e., when a patient is standing, pressure at the foot is communicated to the calf to cause uncomfortable feeling there and, hence, signal to the person of the undesirable foot pressure condition. The device is quite expensive and requires use of special shoes.

While these devices can sense and signal an adverse pressure condition to a patient, they are limited to that function only. Another and equally important condition to which a diabetes patient's feet can be exposed and which a lack of knowledge by the patient can be detrimental to foot well being is temperature. None of the above prior art devices disclose means which sense temperature. If fact, this prior art does not treat of the need for sensing foot temperature as a concern in respect of therapy for treating the feet of diabetes patients.

The significance of signalling a patient as to a foot temperature is that above normal temperature can mean infection, inflammation or analogous symptom indicative of need for remedial action. Where the temperature is low, it could be a sign of frostbite, an occurrence easily brought about by a patients presence in an outside environment of severe cold. Since many diabetes patients lack feeling in their feet, they cannot feel the manifestations in the feet given by the frostbite as such.

Accordingly, it is desirable that there be provided a device which functions to warn a diabetes patient of both adverse pressure and temperature conditions affecting his or her feet.

OBJECTS AND SUMMARY OF THE INVENTION

Accordingly, it is an object of the invention to provide a device for prevention of ulcers in the feet of diabetes patients which overcomes the drawbacks of the prior art.

It is a further object of the invention to provide a device for prevention of ulcers in the feet of diabetes patients which can be embodied in an article of footwear and functions to reliably and accurately sense both a pressure condition and a temperature condition imposed on the feet, and which further readily discernibly signals to a patient advent of a level of one or both of said conditions as are inimical to the well being of the feet.

It is a still further object of the invention to provide a device for prevention of ulcers in the feet of a diabetes patient which readily and conveniently is embodied in various types of footwear.

It is a still further object of the invention to provide a device for prevention of ulcers in the feet of the diabetes patient which detects when a small sharp object has entered the patient's shoe and poses a danger of cutting the patient's foot.

Another object is to provide a device for prevention of ulcers in the feet of a diabetes patient that is relatively inexpensive and thus available to almost all diabetes patients.

Briefly stated, a device for prevention of ulcers in the feet of diabetes patients is embodied in a footwear article such as in a shoe. The device includes a sensor disposed in a contained liquid mass of a hydrocell carried in the shoe inner sole, the sensor being one that detects both pressure and temperature values to which the patient's feet are exposed. The sensor includes a bridge circuit comprised of four piezoresistors arranged in two diagonally arrayed pairs, the resistance of one pair of resistors increasing and the resistance of the second pair decreasing in the presence of an increase in the pressure condition in the hydrocell, the resistance of all the resistors increasing or decreasing responsive to respective increases and decreases of temperature in the hydrocell. Outputs from the bridge circuit denotive of respective pressure and temperature values are acquired by a warning signal generator to operate same to generate a patient discernible warning signal that indicates to the patient a need to take action to avoid continuance of exposure to the condition. A grid array sensor detects localized pressure changes on the bottom of the foot by reducing the resistance between conductors present at the location of the increased pressure. The decreased resistance causes an increase in current flow between the conductors which is detected by a processor which in turn provides an indication of the increased pressure condition.

In accordance with these and other objects of the invention, there is provided for a footwear article having a foot receptive body and an insole disposed in the body, a device for prevention of ulcers in the feet of diabetes patients. The device comprises at least one hydrocell carried in the insole, said hydrocell including a liquid mass and a flexible envelope enclosing the liquid mass. A sensor is disposed in the liquid mass of the hydrocell, the sensor being operable to detect both a pressure condition and a temperature condition present in the hydrocell. The sensor outputs signals indicative of the respective detected pressure and temperature conditions. A signal generator is provided and it receives the respective sensor output signals, the signal generator being operable responsive to said respective sensor output signals to generate patient perceivable warning signals denotive of undesirable pressure and temperature conditions to which a patient's feet should not be exposed. A power cell is provided and it is in circuit with both the sensor and the signal generator for supplying operating power thereto.

Accordingly, there is also provided, a footwear article having a foot receptive body and an insole disposed in said body, a device for the prevention of ulcers in the feet of diabetes patients, said device comprising: upper conductors, mounted in a substantially parallel arrangement on an upper supporting surface, lower conductors, mounted in a substantially parallel arrangement on a lower supporting surface, said upper supporting surface placed on said lower supporting surface such that said upper and lower parallel conductors cross each other forming a grid array, a resistive coating on each of said upper and lower conductors which has the property of reducing a resistance between said upper and said lower conductor when subjected to increased pressure, means for detecting an area of localized pressure imposed on said grid array conductors, and means for alerting said diabetes patient responsive to said means for detecting an area of localized pressure.

The above, and other objects, features and advantages of the present invention will become apparent from the following description read in conjunction with the accompanying drawings, in which like reference numerals designate the same elements.

BRIEF DESCRIPTION OF THE DRAWINGS

FIG. 6 is a perspective view of a grid array sensor, for detecting the presence of small sharp objects in the shoe, showing the upper part being lifted away from the lower part to illustrate the orientation of conductors.

DETAILED DESCRIPTION OF THE PREFERRED EMBODIMENT

The present invention deals with embodiment of a device for prevention of ulcers in the feet of diabetes patients in an article of footwear. While an embodiment of the device will be described as incorporated in a shoe, it will be understood that "footwear" is inclusive of slippers, boots, sandals, etc., since the device readily and conveniently is useable with such footwear items as well.

Figure 1:
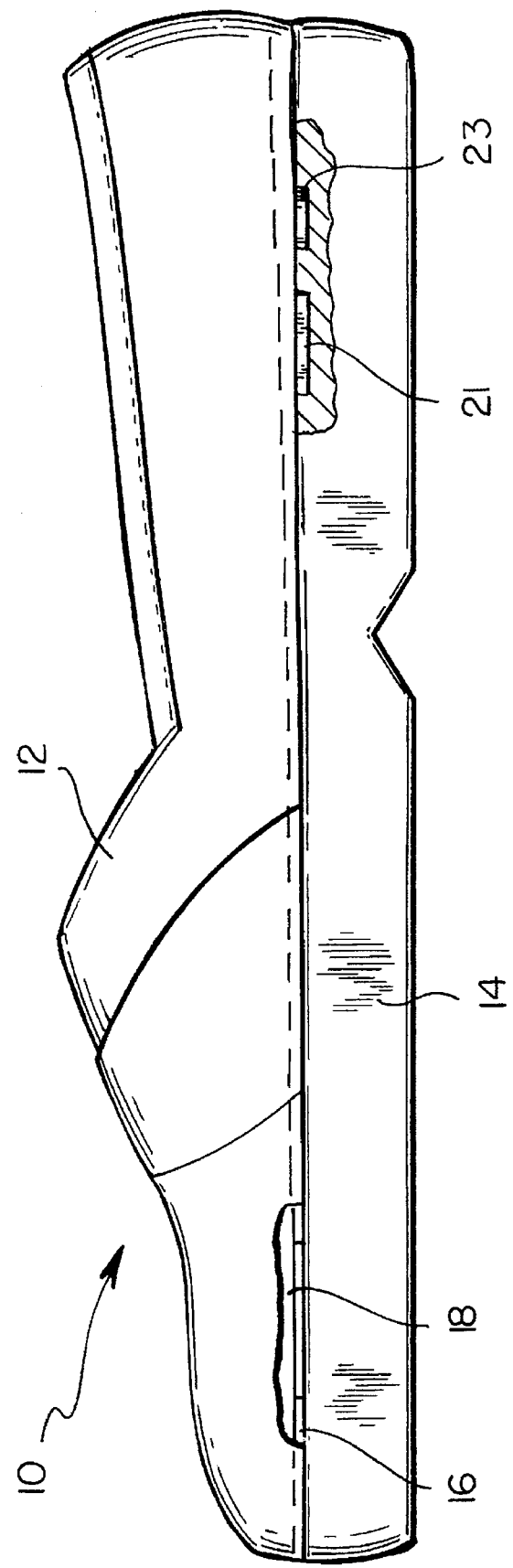
FIG. 1 is a side elevational, diagrammatic depiction, with portions broken away, of a shoe embodying a device for prevention of ulcers of the feet of diabetes patients made in accordance with the principles of the invention.

Referring now to FIG. 1, shoe 10 is of conventional construction having a foot receptive upper or body 12 secured to a solepiece 14, there being an innersole 16 on which, when the shoe is worn, a patient's foot will press.

Figure 5:
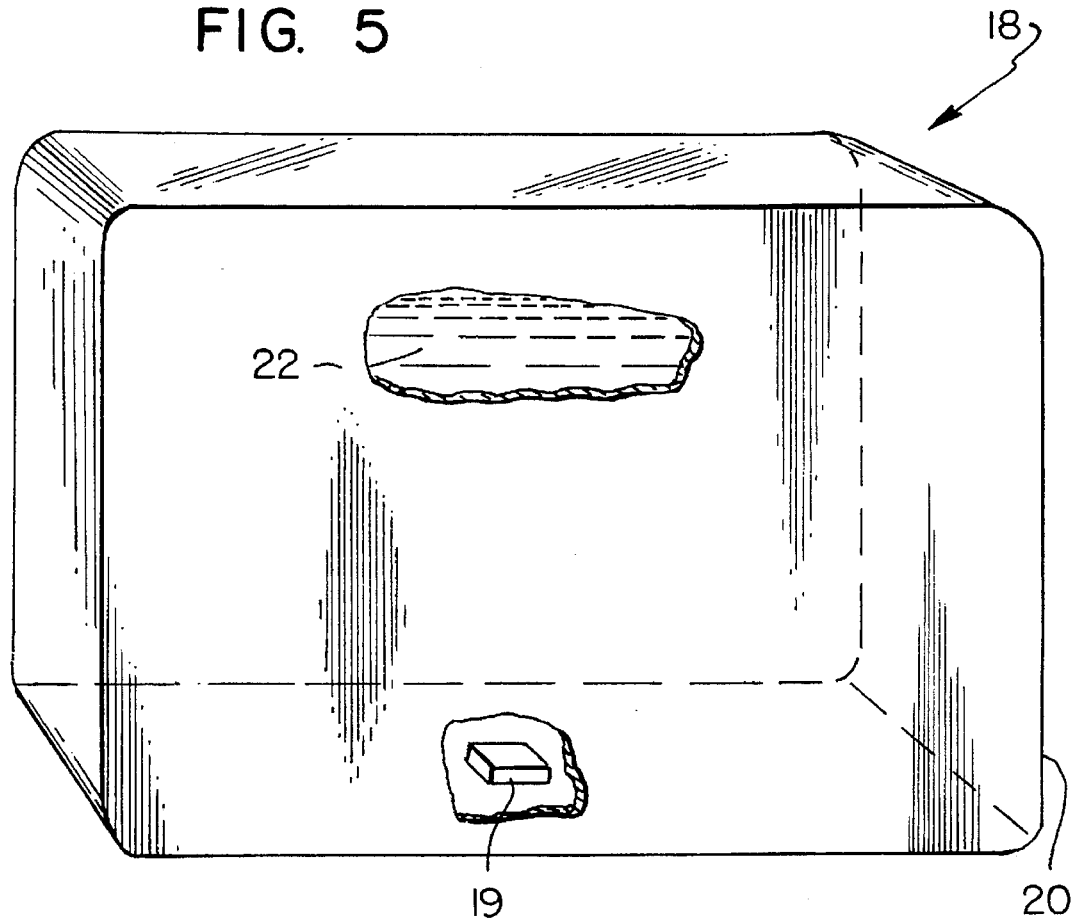
FIG. 5 is a perspective view illustrating the disposition of the sensor within a liquid-filled hydrocell, a part of the hydrocell envelope being broken away to show the disposition of the sensor therein.

Carried at a forepart of innersole 16 is a hydrocell 18. While placement of hydrocell 18 is so depicted and described at the forefront of innersole 16, it should be understood that hydrocell 18 could be located at any number of locations and that plural ones of such hydrocell 18 could be used if desired, if needed, or if beneficial. The hydrocell is a component type commonly known in the art in that it includes, as shown in FIG. 5, a flexible envelope 20 enclosing a liquid mass 22 so that pressure imposed on the envelope by a patient's foot transmits uniformly throughout the hydrocell. Flexible envelope 20 of hydrocell 18 is polyurethane. Liquid mass 22 of hydrocell 18 is silicon-oil. Disposed within the hydrocell is a sensor assembly 19 of the type as will be described below and which is used for detecting both pressure and temperature.

Figure 2:
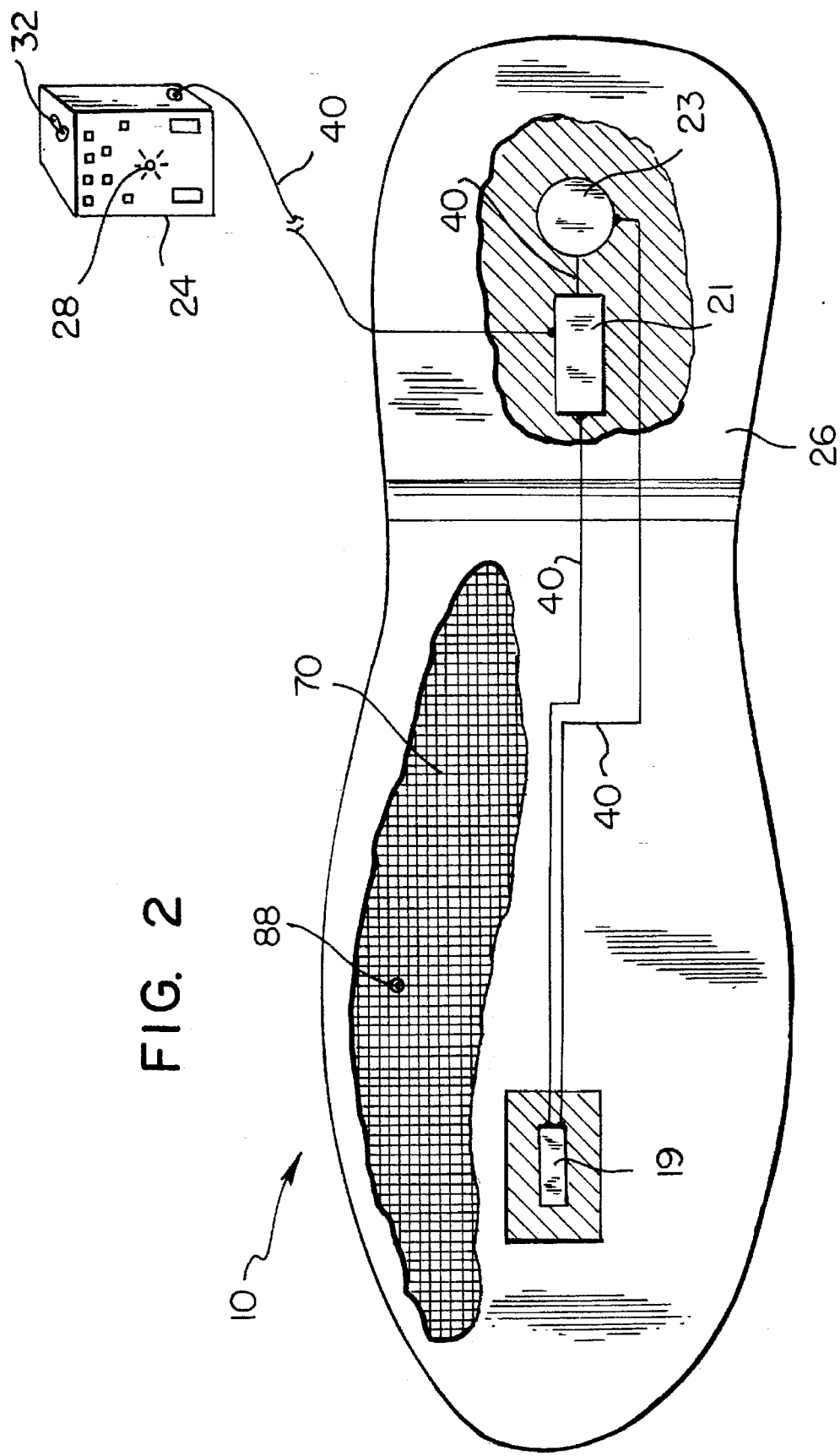
FIG. 2 is a plan depiction of an innersole of the shoe shown in FIG. 1, the device being carried on the innersole.

As seen in FIG. 2, the sensor assembly 19 is in circuit with a warning signal generator 21, a power supply 23 (which can be a constant voltage source such as a battery or a constant current source), and a processor 24, connection being with wiring 40. Warning signal generator 21 and the power supply 23 conveniently are carried in shoe 10, for example, being embodied in a heelpiece 26. In another embodiment warning signal generator 21 is contained within processor 24, at a remote location from shoe 10.

Processor 24, wherein a readily discernible, audible or visual type signaller 28 is located, can be carried by the patient, hooked on to a belt, hung by a strip about the neck or other means as facilitates the patient having the processor in manner as to be made aware of warning signalling. In the preferred embodiment, signaller 28 is a piezo-electric buzzer which converts voltage into soundwaves. Depending on the construction of the footwear and type of signaller 28 used, all of the foregoing components could be carried on the footwear item.

Figure 3A:
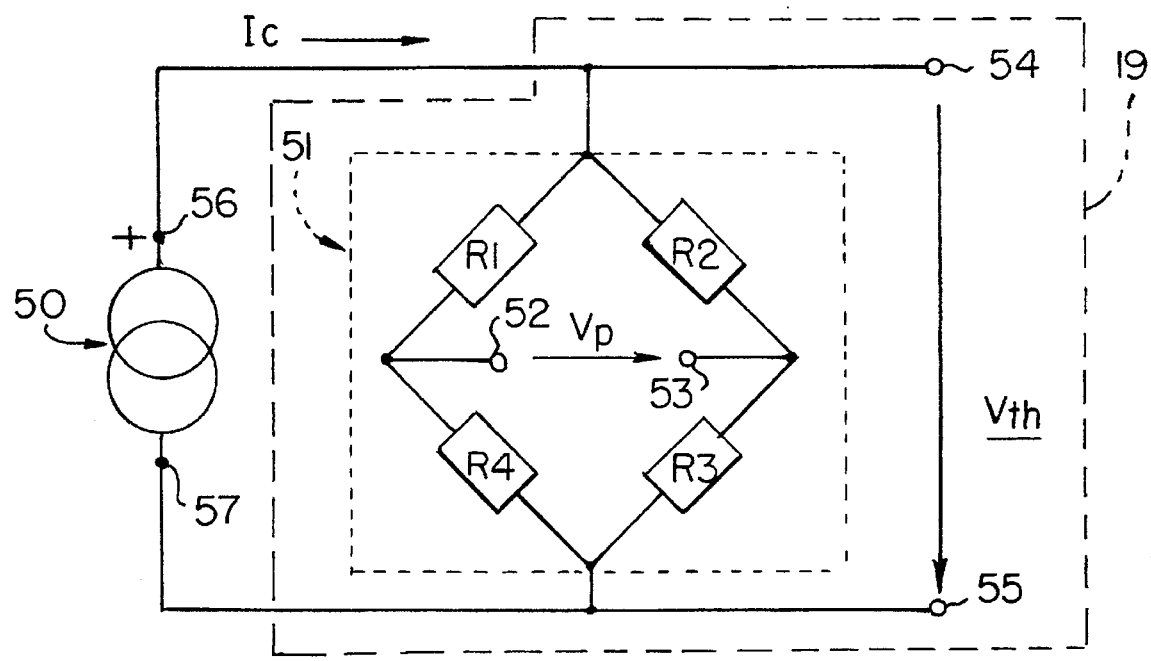
FIG. 3a is a circuit diagram of the pressure/temperature sensor depicting the arrangement therein utilized for sensing pressure values.

Referring now to FIG. 3(a), description is given of the circuit embodiment of sensor assembly 19. Exemplary of sensor assembly 19 is an "Absolute Pressure Sensor 0–7 Bar, AM 767, made by Micronas Semiconductor SA, Switzerland. A positive terminal 56 of a constant current power supply 50 is electrically connected to a terminal 54 of a bridge circuit 51. A negative terminal 57 of the constant current power supply 50 is electrically connected to a terminal 55 of bridge circuit 51. A first resistor R1 and a fourth resistor R4 are serially connected between terminal 54 and terminal 55 of bridge circuit 51. A second resistor R2 and a third resistor R3 are also serially connected between terminal 54 and terminal 55 of bridge circuit 51. Constant current power supply 50 provides a predetermined constant current $I_c$ to bridge circuit 51.

Figure 3B:
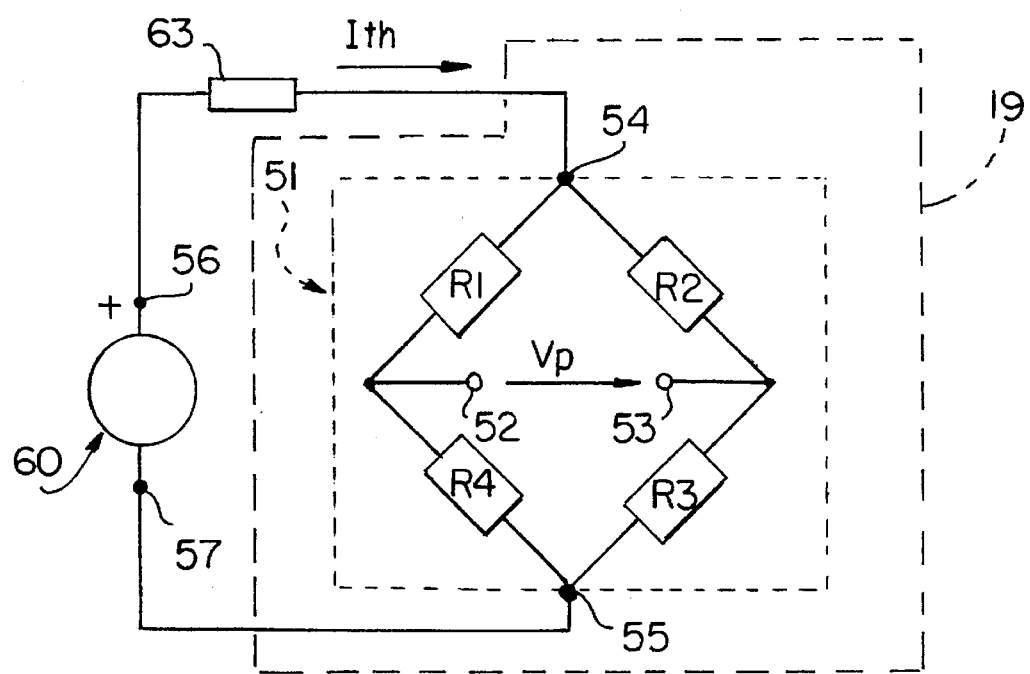
FIG. 3b is a circuit diagram of the pressure/temperature sensor depicting the arrangement therein utilized for sensing temperature.

Referring now also to FIG. 3(b), a constant voltage power supply 60 may be used instead of constant current power supply 50. Constant voltage power supply 60 impresses a constant voltage across terminal 54 and terminal 55.

Figure 4:
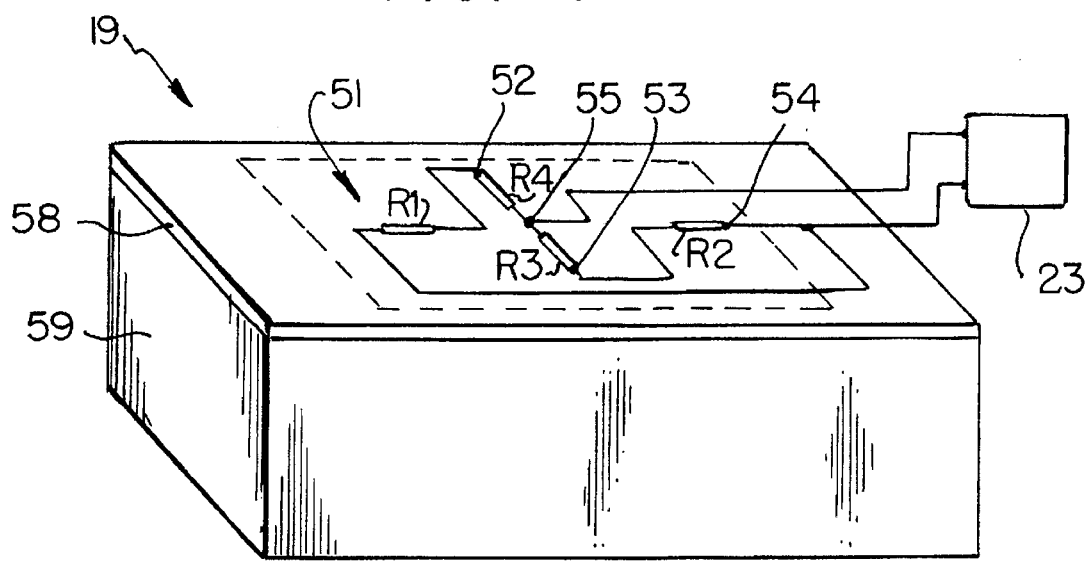
FIG. 4 is a perspective view showing the sensor construction wherein the bridge circuit is carried in a silicon membrane, the membrane being fixed to an evacuated glass chamber structure.

Referring now to FIG. 4, sensor assembly 19 includes first, second, third, and fourth resistors R1, R2, R3, and R4, of bridge circuit 51, etched onto a silicone membrane 58. Bridge circuit 51 receives electrical power from power supply 23 (which can be a constant current power supply 60 or constant voltage supply 50). First, second, third, and fourth resistors R1, R2, R3, and R4 are piezoresistors. The resistivity of a piezoresistor varies in response to deformation of silicon membrane 58. The deformation of silicon membrane 58 is caused by changes in the pressure within hydrocell 18. Silicone membrane 58 is glued onto an evacuated glass chamber 59. In this configuration, first, second, third, and fourth resistors R1, R2, R3, and R4 are exposed to an absolute pressure.

A resistance of first and third resistors R1 and R3 varies in proportion to an amount of pressure applied to silicone membrane 58. A resistance of second and fourth resistors R2 and R4 varies in inverse proportion to an amount of pressure applied to silicone membrane 58. Therefore, if a pressure applied to silicone membrane 58 is increased, the resistance of first and third resistors R1 and R3 increases and the resistance of second and fourth resistors R2 and R4 decreases. Each of the resistors R1, R2, R3, and R4 also varies proportionally with temperature.

Due to the different effects that each of the parameters has on bridge circuit 51, both temperature and pressure can be independently monitored from bridge circuit 51.

Referring now to FIG. 5, sensor assembly 19 is embedded within hydrocell 18. Therefore, first, second, third, and fourth resistors R1, R2, R3, and R4 are responsive to the pressure and temperature present in hydrocell 18.

Referring now again to FIG. 3(a), a first voltage signal $V_{th}$ is measured across terminal 54 and terminal 55. A second voltage signal $V_p$ is measured across terminal 52 and 53. When a pressure applied to hydrocell 18 is increased, first resistor R1 increases in resistance and fourth resistor R4 decreases in resistance resulting in a decrease in voltage potential at terminal 52. In addition, second resistor R2 decreases in resistance and third resistor R3 increases in resistance resulting in an increase in voltage potential at terminal 53. Therefore, second voltage signal $V_p$ changes as the pressure in hydro-cell 62 changes.

The resistances of first, second, third, and fourth resistors R1, R2, R3, and R4 are designed such that a resistance measured across terminals 54 and 55 does not change as the pressure in hydrocell 18 changes (ie. the increase in the resistance of first and third resistors R1 and R3 is equal to the decrease in the resistance of second and fourth resistors R2 and R4). This relationship between the changes in resistance is true because silicone membrane 58 is mounted on evacuated glass chamber 59, which exposes first, second, third, and fourth resistors R1, R2, R3, and R4, on silicone membrane 28, to absolute pressure.

As the temperature increases and decreases, the resistances of each of first, second, third, and fourth resistors R1, R2, R3, and R4 increases and decreases, respectively. Therefore, as the as temperature in hydrocell 18 increases, the resistance measured across terminals 54 and 55 also increases. Because constant current power supply 50 supplies a constant current $I_c$ to bridge circuit 51, first voltage signal $V_{th}$ increases as the temperature and resistance increase. Each resistor R1, R2, R3, and R4 increases an equal proportion of their full value, such that second voltage signal $V_p$ remains constant during a temperature change. Thus, the temperature and the pressure of hydrocell 18 can be monitored separately by first voltage signal $V_{th}$ and second voltage signal $V_p$, respectively.

Referring now to FIG. 3(b), a constant voltage power supply 60 impresses a constant potential across terminal 54 and 55 of bridge circuit 51. Bridge circuit 51 is configured the same as described above. Second voltage signal $V_p$ measures a voltage between terminal 52 and 53 in the same manner as described above. However, because constant voltage power supply 60 impresses a constant voltage at terminals 54 and 55, the voltage between terminals 54 and 55 remains constant when first, second, third, and fourth resistors R1, R2, R3, and R4 change value due to a temperature change in hydrocell 18.

Since the voltage remains constant, a current $I_{th}$ supplied to bridge circuit 51 changes in response to the temperature change instead. A current sensing device 63 is connected between constant voltage power supply 60 and bridge circuit 51 to detect changes in current $I_{th}$ and outputs a third voltage signal $V_I$ which is proportional to $I_{th}$. As described above, first, second, third, and fourth resistors R1, R2, R3, and R4 are designed to react to absolute pressure such that the increase in resistance of first and third resistors R2 and R3 the decrease resistance of second and fourth resistors R2 and R4 are equivalent such that the resistance measured between terminal 54 and terminal 55 remains constant for a change in pressure applied to hydrocell 18. Consequently, current $I_{th}$ remains constant as well for a change in pressure applied to hydrocell 18.

Referring now to FIGS. 2 and 3(a), warning signal generator 21 monitors first voltage signal $V_{th}$ and second voltage signal $V_p$. If the embodiment in FIG. 3(b) is used, warning signal generator 21 monitors second voltage signal $V_p$ and third voltage signal $V_I$. Using one or more solid state switching circuits, such as, for example, an SCR, a BJT, a diode, or a UJT, warning signal generator 21 acts as a switch which transmits an open or closed signal recognizeable by processor 24. Warning signal generator 21 compares second voltage signal $V_p$ against a preset maximum pressure signal and compares $V_{th}$ or $V_I$ against a preset maximum temperature and a preset minimum temperature. Warning signal generator 21 transmits a closed signal when any one of these parameters reaches an adverse condition (ie. when pressure is greater than the preset maximum pressure signal, when temperature is greater than the preset maximum temperature signal, or when temperature is less than the present minimum temperature signal). Processor 24 turns on or off signaller 28 responsive to a closed or open signal respectively, to alert the user of the adverse pressure or temperature condition. Warning signal generator 21 can monitor one or all three of these parameters.

In another embodiment, processor 24 receives signals from the sensor unit directly which are indicative of foot pressure and temperature at the foot conditions so that where such conditions are inimical to the patient, signal to the patient occurs. Further, because the signals from the sensor are sent directly to processor 24, a record of data dealing with pressure and temperature conditions over a period can be recorded and made available to the patient's physician.

The person skilled in art will also understand that exposure of a patient's feet to the different activities of walking and running can require program shift in the processor from walk to run mode. To prevent nuisance alarms during periods of increased physical activity, such as running, the sensitivity of the warning signal generator can be adjusted. This can be effected by a patient operated switch 32 carried on processor 24 for selectively switching between two or more modes of operation. In addition, more complex algorythms can be used, such as, for example, pre-calculating programs which calculate an alarm setpoint based on parameters such as the patient's weight and the type of activity.

Referring now to FIGS. 2 and 6, another type of pressure detection device is a grid array sensor 70 for detecting the presence of small sharp objects which present a danger to the patient of causing a cut or sore due an intense localized pressure. Grid array sensor 70 includes upper conductors 73 arranged substantially parallel on an upper supporting surface 71 and lower conductors 74 arranged substantially parallel on a lower supporting surface 72. Upper and lower conductors 73 and 74 are placed substantially perpendicular to each other to form a grid.

Each of upper conductors 73 and lower conductors 74 has a resistive coating, the resistance of which is substantially reduced when pressure is applied to it. Power supply 23 impresses a voltage potential between upper conductors 73 and lower conductors 74. Therefore a minimal current passes between upper conductors 73 and lower conductors 74. The reduction in resistance of the resistive coating, due to an increased pressure, allows a greater current to pass between at least one upper conductor 73 and at least one lower conductor 74 than when normal pressure is present.

Grid array sensors 70 are disclosed in greater detail in U.S. Pat. No. 4,734,034 and U.S. Pat. No. 4,856,993 and for purposes of elaboration thereon, such disclosures are incorporated herein by reference. Specifically, FIGS. 1–3 and the text beginning at column 3, line 9, through column 6, line 9, of U.S. Pat. No. 4,734,034 and FIGS. 1–3 and the text beginning at column 3, line 15, through column 4, line 56 of U.S. Pat. No. 4,856,993 are included by reference.

When a small sharp object, such as a pebble 88 (see FIG. 2), is accidentally present within shoe 10 and such can constitute a wound producing agency, such objects also including small stones, broken glass, etc., localized pressure on grid array sensor 70, where the sharp object is located, causes the resistance between at least one upper conductor 73 and at least one lower conductor 74 to decrease, thereby increasing the current through the affected upper conductor 73 and lower conductor 74. The increased current flow can be detected by processor 24. Processor 24 monitors each individual conductor and when an increased current is detected, surpassing a predetermined threshold value, processor 24 alerts the user that there is a localized pressure condition. Processor 24 optionally shows where in the shoe the localized pressure is located based on which specific upper and lower conductors 73 and 74 are affected.

Grid array sensor 70 generally can be made to conform with the plan shape of innersole 16 and is installed in shoe 10 on top of, or below, innersole 16. In another embodiment, innersole 16 is grid array sensor 70. Other plan geometries of pans of the patient's sole can be used if desired and/or advantageous. When the patient is wearing shoe 10, grid array sensor 70 is between innersole 16 and patient's foot. In this manner grid array pressure sensor monitors the pressure on the bottom surface of the patient's foot.

Grid array sensor 70 can be used alone to detect any harmful pressures or it can be used in conjunction with the hydrocell and sensor assembly described above. In the latter configuration, the hydrocell and sensor assembly can be calibrated to detect relatively long term high pressure in shoe 10 and abnormal temperature conditions. The grid array pressure sensor can then be calibrated to detect presence of small sharp objects which constitute a wound producing agency. The small sharp objects can be a risk to a patient because they can create enough localized pressure to cause a cut or sore to the foot in a short time.

The combination of both hydrocell 18 and grid array pressure sensor 70 provide a high degree of protection against both long term high pressure and abnormal temperature conditions and against sharp localized pressure caused by foreign objects which enter shoe 10.

Having described preferred embodiments of the invention with reference to the accompanying drawings, it is to be understood that the invention is not limited to those precise embodiments, and that various changes and modifications may be effected therein by one skilled in the art without departing from the scope or spirit of the invention as defined in the appended claims.

What is claimed is:

1. In a footwear article having a foot receptive body and an insole disposed in the body, a device for prevention of ulcers in the feet of diabetes patients, said device comprising
at least one hydrocell carried in said insole, said hydrocell including a liquid mass and a flexible envelope enclosing said liquid mass,
a sensor disposed in the liquid mass of said hydrocell, said sensor being operable to detect both a pressure condition and a temperature condition present in the hydrocell and output respective signals indicative of detected pressure and temperature conditions,
a signal generator receiving the respective sensor output signals and operable responsive to said respective sensor output signals to generate patient perceivable warning signals denotive of undesirable pressure and temperature conditions to which a patient's feet should be exposed, and
a power cell in circuit with both said sensor and said signal generator for supplying operating power thereto.

2. The footwear article of claim 1 in which the signal generator and the power cell are carried in said body.

3. The footwear article of claim 1 in which said sensor includes a four-terminal bridge circuit further comprising four piezoresistive type resistors connected in two diagonally arranged pairs, the resistance of one pair of resistors increasing and the resistance of the second pair decreasing in the presence of and increase in the pressure condition in the hydrocell, and the resistance of all the resistors increasing or decreasing responsive to respective increases and decreases in temperature in said hydrocell.

4. The footwear article of claim 1 in which said sensor includes:
an electrical bridge circuit having a first, second, third, and fourth terminals;
first and third piezoresistors with a resistance that increases in the presence of an increase in pressure in the hydrocell; and second and fourth piezoresistors with a resistance that decreases in the presence of an increase in pressure in the hydrocell;

each of said first, second, third, and fourth piezoresistors having a resistance that increases or decreases responsive to respective increases and decreases of temperature in said hydrocell;

said first piezoresistor connected between said first terminal and said second terminals;

said second piezoresistor connected between said second terminal and said third terminal;

said third piezoresistor connected between said third terminal and said fourth terminal; and said fourth piezoresistor connected between said fourth terminal and said first terminal.

5. The footwear article of claim 4, further including:

means for receiving and applying a constant voltage potential across said first terminal and said third terminal;

means for detecting a pressure change in said hydrocell responsive to a means for monitoring voltage across second and fourth terminals; and means for detecting a temperature change in said hydrocell responsive to means for monitoring an electric current to said electrical bridge.

6. The footwear article of claim 4, further including:

means for receiving and applying a constant electrical current to said bridge circuit;

means for detecting a pressure change in said hydrocell responsive to a means for monitoring voltage across said second terminal and said fourth terminal; and means for detecting a temperature change in said hydrocell responsive to means for monitoring voltage across said first terminal and said third terminal.

7. The footwear article of claim 4, wherein:

said first, second, third, and fourth piezoresistors are etched onto a semiconductor membrane and said semiconductor membrane is fixed to an evacuated glass chamber such that said first, second, third, and fourth piezoresistors are exposed to an absolute pressure.

8. The footwear article of claim 1, further including a second sensor comprising:

upper conductors, mounted in a substantially parallel arrangement on an upper supporting surface;

lower conductors, mounted in a substantially parallel arrangement on a lower supporting surface;

said upper supporting surface being disposed on said lower supporting surface such that said upper and lower parallel conductors cross each other forming a grid array; and a resistive coating on each of said upper and lower conductors which has the property of reducing resistance when subjected to pressure;

said second sensor being operable to detect an area of localized pressure imposed on said grid array conductors and output a signal to operate said signal generator.

9. The footwear article of claim 8, wherein said lower conductors are oriented substantially perpendicular to said upper conductors.

10. The footwear article of claim 9, further including:

means for receiving and applying a voltage potential between said upper conductors and said lower conductors;

means for detecting an increase in current between at least one of said upper conductors and at least on of said lower conductors responsive to an increased pressure where said at least one of said upper conductors crosses said at least one of said lower conductors.

* * * * *